United States Patent [19]

Koshimizu et al.

[11] Patent Number: 4,862,383
[45] Date of Patent: Aug. 29, 1989

[54] ULTRASONIC INSPECTION APPARATUS

[75] Inventors: Chishio Koshimizu, Yamanashi; Yasuo Hayakawa; Toshio Nonaka, both of Ibaraki; Sakae Takeda, Tsuchiura, all of Japan

[73] Assignee: Hitachi Construction Machinery Co., Ltd., Tokyo, Japan

[21] Appl. No.: 919,766

[22] Filed: Oct. 16, 1986

[30] Foreign Application Priority Data

Oct. 16, 1985 [JP] Japan ................................ 60-228778

[51] Int. Cl.$^4$ ............................................ G01N 29/04
[52] U.S. Cl. ...................................... 364/507; 73/600; 73/606; 73/632
[58] Field of Search ................... 364/506, 507; 73/599, 73/602, 606, 624, 625, 627–629, 632, 633, 600

[56] References Cited

U.S. PATENT DOCUMENTS

| | | | |
|---|---|---|---|
| 4,213,183 | 7/1980 | Barron et al. | 364/507 |
| 4,327,588 | 5/1982 | North | 364/507 |
| 4,462,082 | 7/1984 | Thiele et al. | 364/507 |
| 4,475,398 | 10/1984 | Tjornhos et al. | 73/599 |

Primary Examiner—Parshotam S. Lall
Assistant Examiner—Brian M. Mattson
Attorney, Agent, or Firm—Antonelli, Terry & Wands

[57] ABSTRACT

In an ultrasonic inspection method and apparatus for inspecting the presence or absence of a defect in an object to be inspected by receiving as an RF signal a reflection beam of an ultrasonic beam emitted from a probe to the object and displaying data of the RF signal on a display unit, a maximum value indicative of a positive peak of the RF signal is detected, a maximum absolute value indicative of a negative peak of the RF signal is detected, a computation is performed for comparing in magnitude the maximum value indicative of the positive peak with the maximum absolute value indicative of the negative peak, and a computed value is displayed on the display unit so that the presence or absence of a phase inversion of the RF signal may be judged for deciding the presence or absence of a defect in the object.

9 Claims, 6 Drawing Sheets

SOUND BONDING PORTION (A)

EXFOLIATED BONDING PORTION (A)

(B)

(C)

ULTRASONIC INSPECTION APPARATUS

BACKGROUND OF THE INVENTION

This invention relates to an ultrasonic inspection method and apparatus for detecting the presence or absence of defects in an object to be inspected and more particularly to an ultrasonic inspection method and apparatus suitable for examining the presence or absence of exfoliation at a bonding portion between two bodies and the presence or absence of voids in a body.

Demands for accurate and easy inspection of the presence or absence of exfoliation at a bonding portion at the interface between bodies and a void in a body have come out of various fields of technologies. Recently, these demands have been accelerated especially because a variety of electronic parts such as IC packages and various products incorporating electronic parts have been put in production and exfoliation at bonding portions and voids in bodies seriously affect performance and function of these parts and products.

In the past, as one of the methods for inspection of defects in electronic parts, an ultrasonic inspection method has been known wherein an object to be examined is immersed in a liquid vessel (typically a water vessel), an ultrasonic beam is emitted to the object from a probe also immersed in the liquid vessel, a reflecting beam from a portion of the object, for example, a bonding portion is received and converted into an RF signal, and the RF signal is displayed on a display unit to indicate the presence or absence of a defect.

In displaying RF signals on a display unit, two methods are available of which one is termed an A-scope display in which changes in amplitude of an RF signal waveform traced on the ordinate of an oscilloscope is displayed relative to the time traced on the abscissa and the other is termed a C-scope display in which a maximum value indicative of a positive peak of an RF signal waveform or a maximum in absolute value indicative of a negative peak of the RF signal waveform is produced by scanning a probe vertically and horizontally with respect to an object to be examined and is displayed in the form of a gradation display on a monitor television whose abscissa represents a moving distance of the probe in the horizontal direction (X) and ordinate represents a moving distance in the vertical direction (Y).

When an object to be inspected has a defect such as a peeled off bonding portion or a void, an ultrasonic beam is reflected approximately 100% at such a defective interface as above and the level of the reflecting beam becomes larger than that of a reflecting beam from a portion without any defect. In nature, the phase of a reflecting beam originating from an ultrasonic beam which comes into a material of a small acoustic impedance (represented by the product of density of the material and sound velocity) from a material of a large acoustic impedance undergoes inversion. Therefore, the phase of a reflecting beam from a defect such as a peeled off bonding portion or a void is inverted relative to the phase of a reflecting beam from a non-defective portion and, given the phase of the latter reflecting beam being positive, the phase of the former reflecting beam becomes negative.

Conventionally, in the A-scope display method, the inspector makes a decision empirically using the above-mentioned two natures of the ultrasonic beam as an evaluation index. In the C-scope display method, the inspector also makes a decision empirically by observing a density pattern in a resulting gradation display utilizing the former nature of the ultrasonic beam. One may refer to a relevant application, i.e., U.S. Pat. No. 4,768,155 or corresponding European Patent Application No. 86100581.7.

The aforementioned two natures of the ultrasonic beam, however, are not always clearly developed for any type of exfoliation and void. Even with the signal waveform from, for example, exfoliation, its level will sometimes increase indistinctively slightly and its phase will not sometimes be inverted distinctively. Accordingly, the conventional inspection methods which relied upon the empirical judgement by the inspector can not be well adapted for such critical events as above because the magnitude of the waveform level and/or the presence or absence of the phase inversion can not be judged correctly and even if possible, the judgement is considerably time consuming.

Further, if waveform levels from bonding portions of different examined objects are equal to each other, it is difficult to judge whether the same waveform level indicates normal bonding or exfoliation of abnormal bonding.

SUMMARY OF THE INVENTION

An object of this invention is to provide an ultrasonic inspection method and apparatus capable of detecting accurately and quickly the presence or absence of defects in an object to be inspected, especially, the presence or absence of exfoliation at a bonding portion or a void in a body.

The present inventors have conducted a variety of experiments on ultrasonic reflecting beams and have observed the fact that when a maximum value indicative of a positive peak is compared with a maximum in absolute value indicative of a negative peak in connection with a waveform of a typical reflecting beam of non-inverted phase produced from an inspection object without any defect such as exfoliation at a bonding portion, the maximum value indicative of the positive peak is larger than the maximum absolute value indicative of the negative peak whereas when a similar comparison is performed in connection with a waveform of a typical reflecting beam of inverted phase produced from an inspection object with a defect such as exfoliation at a bonding portion, the maximum absolute value indicative of the negative peak is larger. Based on the above fact, the present inventors have determined that the presence or absence of a defect can be detected by comparing in magnitude a maximum value indicative of a positive peak of a reflecting beam with a maximum absolute value indicative of a negative peak of the reflecting beam so as to judge the presence or absence of a phase inversion. Further, experiments conducted by the present inventors have indicated that the phase inversion may occur depending on the kind of an object to be inspected if a maximum value indicative of a positive peak is slightly larger than a maximum absolute value indicative of a negative peak, and that introduction of a threshold value experimentally determined for every kind of the inspection object can permit more accurate judgement of the presence or absence of a phase inversion.

This invention has been achieved by acknowledging the above-mentioned novel technical knowledge found out by the present inventors.

According to one aspect of the present invention, there is provided an ultrasonic inspection method for inspecting the presence or absence of a defect in an object to be inspected by receiving as an RF signal a reflection beam of an ultrasonic beam emitted from a probe to the object and displaying data of the RF signal on a display unit, the inspection method comprising the steps of detecting a maximum value indicative of a positive peak of the RF signal, detecting a maximum absolute value indicative of a negative peak of the RF signal, performing a computation for comparing in magnitude the maximum value indicative of the positive peak with the maximum absolute value indicative of the negative peak, and displaying a computed value on the display unit so that the presence or absence of a phase inversion of the RF signal may be judged for deciding the presence or absence of a defect in the object.

According to another aspect of the invention, there is provided an ultrasonic inspection apparatus having a probe for emitting an ultrasonic beam to an object to be inspected, a pulser for transmitting to the probe a pulse signal necessary for generation of the ultrasonic beam, a receiver for receiving a reflection beam of the ultrasonic beam from the object and generating an RF signal corresponding to the reflection beam and a display unit for displaying data of the RF signal to allow the presence or absence of a defect in the object to be judged on the basis of contents displayed on the display unit, the inspection apparatus comprising a peak detector, connected to the receiver, for detecting a maximum value indicative of a positive peak of the RF signal and a maximum absolute value indicative of a negative peak of the RF signal, and a controller, connected to the peak detector, for performing a computation for comparing in magnitude the maximum value indicative of the positive peak with the maximum absolute value indicative of the negative peak and transmitting a computed value to the display unit to cause the computed value to be displayed thereon.

DESCRIPTION OF THE PREFERRED EMBODIMENTS

Figure 1:
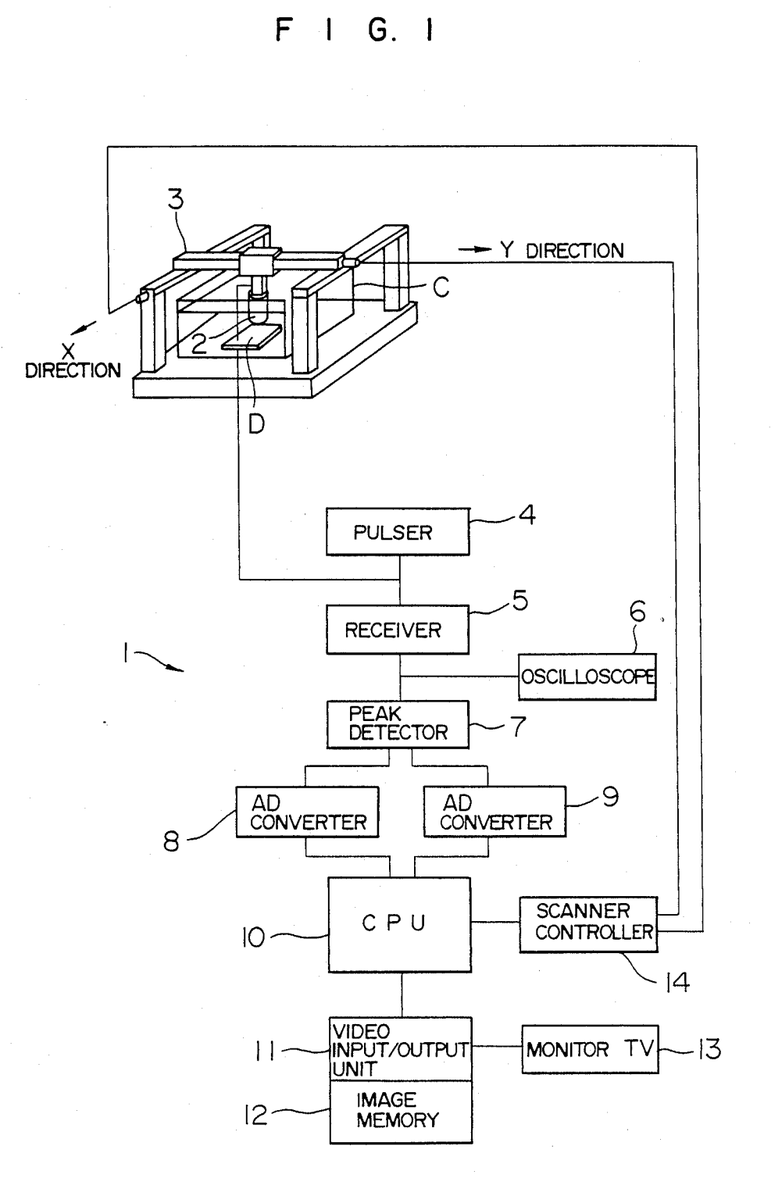
FIG. 1 is a schematic block diagram showing an ultrasonic inspection apparatus according to an embodiment of the invention.

Referring now to FIG. 1, there is illustrated an ultrasonic inspection apparatus, generally designated at reference numeral 1, according to a preferred embodiment of the invention. The apparatus 1 has a probe 2 for emitting an ultrasonic beam to an object D to be inspected which is placed on the bottom of a vessel C containing water. The probe 2 is carried by a scanning unit 3 so as to be movable relative to the object D in orthogonal directions, i.e. X and Y directions.

The probe 2 is connected to a pulser 4 which transmits to the probe 2 a pulse signal necessary for generation of an ultrasonic beam, and to a receiver 5 which receives a reflecting beam from the object D and generates an RF signal corresponding to the reflecting beam. Connected to the receiver 5 is an oscilloscope 6 for displaying the RF signal in A-scope display fashion.

The receiver 5 is also connected with a peak detector 7 adaped to detect a maximum value P indicative of a positive peak of the RF signal and a maximum absolute value N indicative of a negative peak of the RF signal. As will be described later, the peak detector 7 produces an output signal containing a DC voltage proportional to the maximum value P indicative of the positive peak and an output signal containing a DC voltage proportional to the maximum absolute value N indicative of the negative peak. These DC voltages are converted by AD converters 8 and 9, respectively, into digital signals which in turn are applied to a CPU 10.

Figure 2:
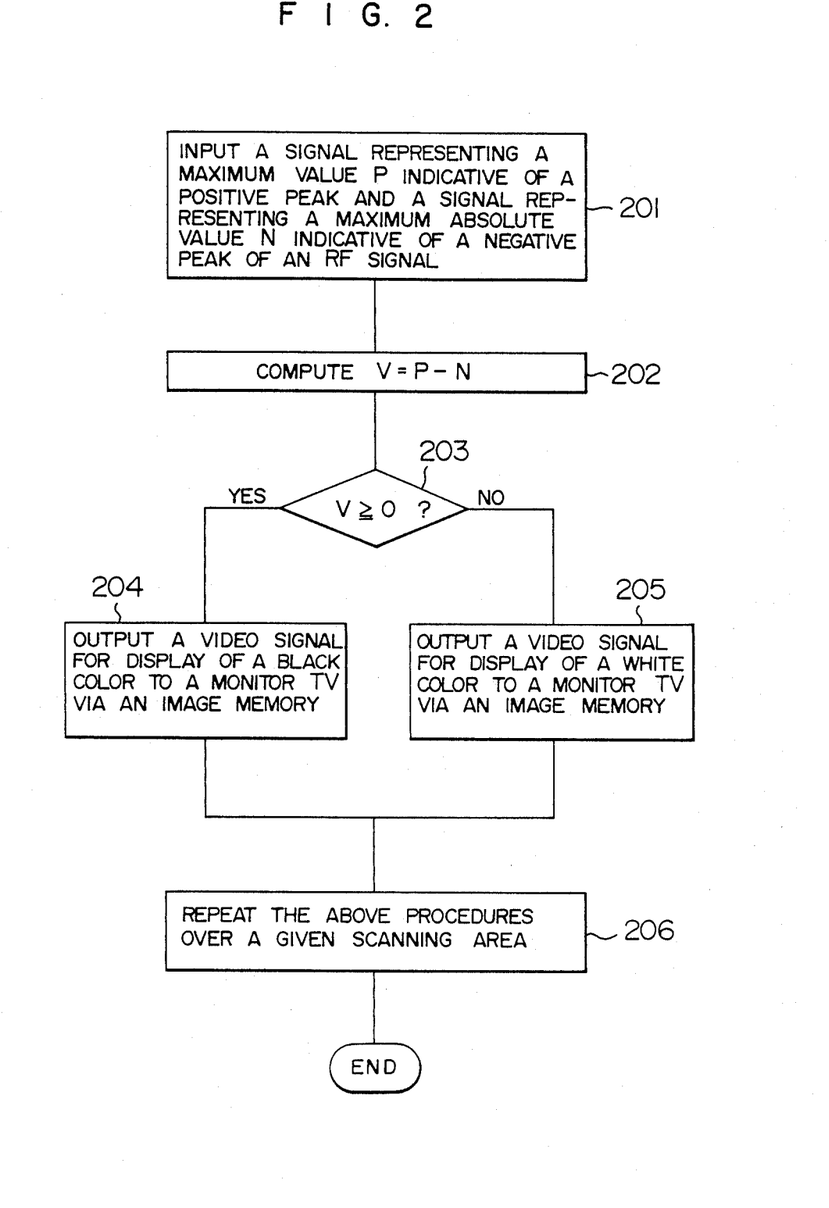
FIG. 2 is a flow chart illustrating an essential part of controlling performed by a CPU included in the ultrasonic inspection apparatus shown in FIG. 1.

The CPU 10 is programmed as shown in FIG. 2. More particularly, the CPU 10 is inputted with the signals respectively representing the maximum value P indicative of the positive peak and the maximum absolute value N indicative of the negative peak (step 201) and thereafter, it performs a computation for comparing in magnitude these maximum values (step 202). In an illustrated embodiment, the latter maximum value is subtracted from the former maximum value. The CPU 10 then judges the polarity of a computed value V (step 203) and produces, as a video signal, a binary signal in accordance with a decided polarity or a multi-coded signal in accordance with the decided polarity and the level of the computed value V. In this embodiment, when the computed value V is positive, a video signal is prepared for displaying a black color on a monitor television 13 (step 204) and when negative, a video signal for displaying a white color is prepared (step 205).

The video signal is applied to a video input/output unit 11 connected to the CPU 10. The video input/output unit 11 is connected with an image memory 12 and the monitor television 13 so that the video signal transmitted from the CPU 10 is once stored in the image memory 12 and delivered therefrom to the monitor television 13 in synchronism with horizontal and vertical scanning signals for the television 13.

The CPU 10 is also connected with a scanner controller 14 which drives the scanning unit 3 in the manner described previously, whereby video signals can be obtained over a given scanning area on the object D and hence a C-scope display based on these video signal can be displayed on the display screen of the monitor television 13. The scanner controller 14 itself and a control program of the CPU 10 for the controller 14 are known in the common ultrasonic inspection method based on C-scope display and will not be detailed herein.

Figure 3:
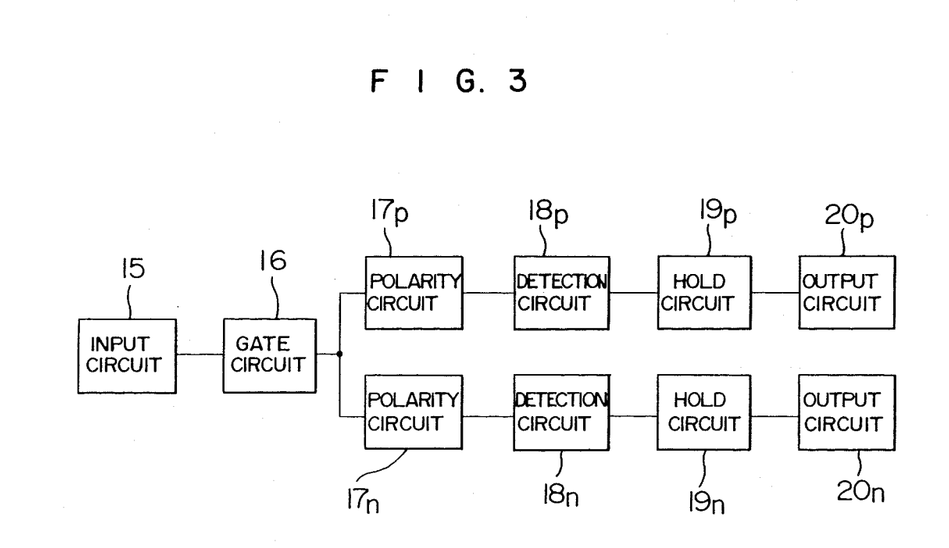
FIG. 3 is a block diagram illustrating details of a peak detector included in the apparatus of FIG. 1.

Referring to FIG. 3, the peak detector 7 comprises an input circuit 15 for receiving an RF signal delivered out of the receiver 5, a gate circuit 16 operative to open a gate to pass the RF signal for a predetermined time after expiration of a predetermined delay time so that only a portion of the input RF signal representative of a reflection beam from an inspection portion of the object may be picked up, a first polarity circuit 17p for passage of only a positive-going waveform of the RF signal passed through the gate circuit and a second polarity circuit 17n for passage of only a negative-going waveform of the passed RF signal, first and second detection circuits 18p and 18n for detecting the positive-going and negative-going waveforms passed through the first and second polarity circuits 17p and 17n, respectively, first and second hold circuits 19p and 19n for holding maximum values of waveforms detected by the first and secnd detection circuits, respectively, and output circuits 20p and 20n for respectively delivering DC voltages proportional to the maximum values of waveforms held by the hold circuits 19p and 19n. This arrangement permits detection of a maximum value indicative of a positive peak and a maximum absolute value indicative of a negative peak of the RF signal.

Figure 4:
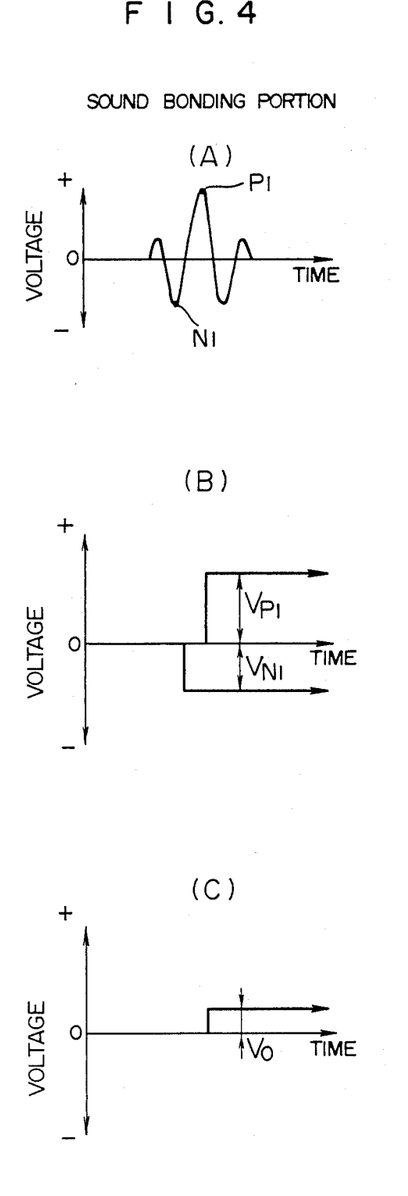
FIGS. 4(A)-4(C) illustrate an RF signal, a DC voltage output from the peak detector and a difference computed by the CPU which are obtained from a bonding portion without exfoliation of an object.

With the ultrasonic inspection apparatus constructed as above, given a waveform as shown in FIG. 4(A) representative of an RF signal set from the receiver 5 and passed through the gate circuit 16 of the peak detector 7, the first circuits 17p, 18p and 19p cooperate together to detect a maximum value P1 indicative of a positive peak, the second circuits 17n, 18n and 19n cooperate together to detect a maximum absolute value N1 indicative of a negative peak, and the output circuits 20p and 20n deliver DC voltages VP1 and VN1 as shown in FIG. 4(B). These DC voltages are digitized by the AD converters 8 and 9 and then inputted to the CPU 10 which in turn computes VP1−VN1 to provide a computed value Vo as shown in FIG. 4(C).

Then, the CPU 10 judges the polarity of the computed value Vo. Since, in this example, the computed value Vo is positive, the CPU 10 prepares a video signal for displaying a black color, for example, on the screen of the monitor television 13 and delivers the video signal to the monitor television 13 through the image memory 12.

The positive polarity of the computed value Vo indicates that the maximum value P1 indicative of the positive peak of the RF signal is larger than the maximum absolute value N1 indicative of the negative peak, and that pursuant to the aforementioned novel knowledge determined by the present inventors, the phase of the RF signal is positive being affected by phase inversion, thus indicating that an inspected portion of the object, for example, a bonding portion is not exfoliated in view of the previously-described natures of the ultrasonic beam.

Figure 5:
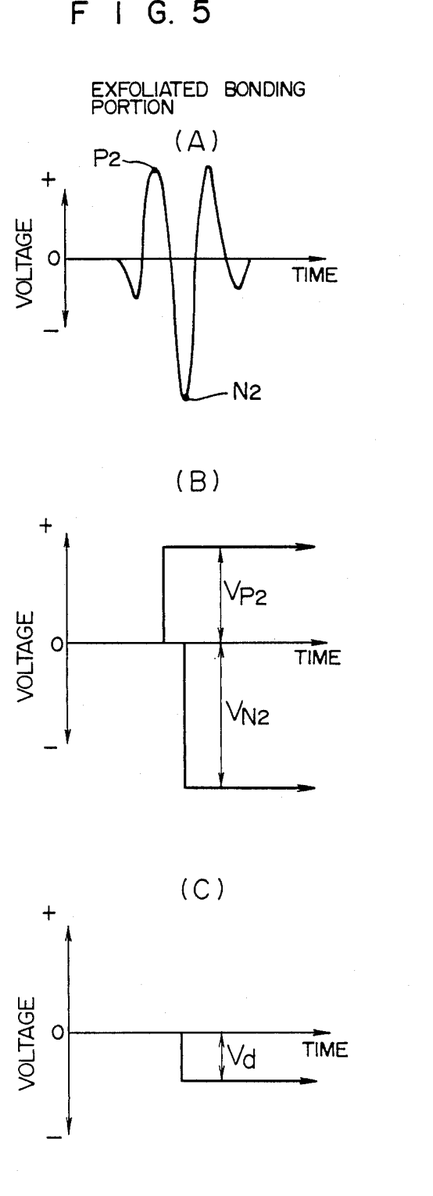
FIGS. 5(A)-5(C) illustrate waveforms similar to those of FIGS. 4(A)-4(C), but obtained from a bonding portion with exfoliation of an object.

Next, given a waveform in FIG. 5(A) representative of an RF signal sent from the receiver 5 and passed through the gate circuit 16 of the peak detector 7, the peak detector 7 likewise detects a maximum value P2 indicative of a positive peak and a maximum absolute value N2 indicative of a negative peak of the RF signal to produce DC voltages VP2 and VN2 in FIG. 5(B) which are proportional to the maximum values, and these DC voltages are digitized by the AD converters 8 and 9, whereby the CPU 10 then computes VP2−VN2 and judges the polarity of a computed value Vd, which is negative in this example in FIG. 5(C), leading to a video signal for displaying a white color, for example, on the screen of the monitor television 13, the video signal being delivered to the image memory 12 and monitor television 13.

The negative polarity of the computed value Vd indicates that the maximum absolute value N2 indicative of the negative peak of the RF signal is larger than the maximum value P2 indicative of the positive peak, and that pursuant to the novel knowledge determined by the present inventors, the phase of the RF signal is negative and inverted, thus indicating that an inspected portion of the object, for example, a bonding portion is exfoliated in view of the previously-described natures of the ultrasonic beam.

By preparing video signals over a given scanning area on the object D and supplying the video signals to the monitor television 13 in this manner, a C-scope display of an inspected portion of the object can be obtained in which a normal portion of the object without such a defect as exfoliation at a bonding portion is displayed with black and a defective portion such as a peeled off bonding portion is displayed with white. Even an inexpert inspector can therefore examine the presence or absence of a defect with ease and quickness.

It has been described in the preceding that even when a maximum value indicative of a positive peak exceeds a maximum absolute value indicative of a negative peak of an RF signal, this RF signal, if the excess is slight, sometimes stems in fact from a reflection beam from a defect such as an exfoliated bonding portion depending on the kind of an object to be inspected and the phase of that RF signal is eventually inverted. It is therefore convenient to introduce a threshold $\alpha$ experimentially determined for each kind of object into the comparison of the maximum value indicative of the positive peak with the maximum absolute value indicative of the negative peak.

Specifically, given the positive peak maximum value of the RF signal being P and the negative peak maximum absolute value being N, $V = P - (N + \alpha)$ is computed, and the absence of a defect such as exfoliation is judged from a positive V and the presence of a defect is judged from a negative V. For the sake of performing this judgement with the ultrasonic inspection apparatus 1, the program of the CPU 10 may simply be modified such that $V = P - (N + \alpha)$ is computed and a binary video signal corresponding to a positive or negative polarity of V or a multi-coded video signal for gradation display depending on the polarity and level of V is then produced.

Although in the previous embodiment the positive peak maximum value of the RF signal is compared in magnitude with the negative peak maximum absolute value by subtracting the latter from the former, the ratio of the former to the latter may be computed for comparison. In such a comparison, when the computed value is greater than 1 (one), the maximum value indicative of the positive peak is larger indicating that the phase is not inverted and the inspection portion such as a bonding portion is sound, but when the computed value is less than 1 (one), the maximum absolute value indicative of the negative peak is larger indicating that an inspection portion such as a bonding portion is defective or exfoliated.

Figure 6:
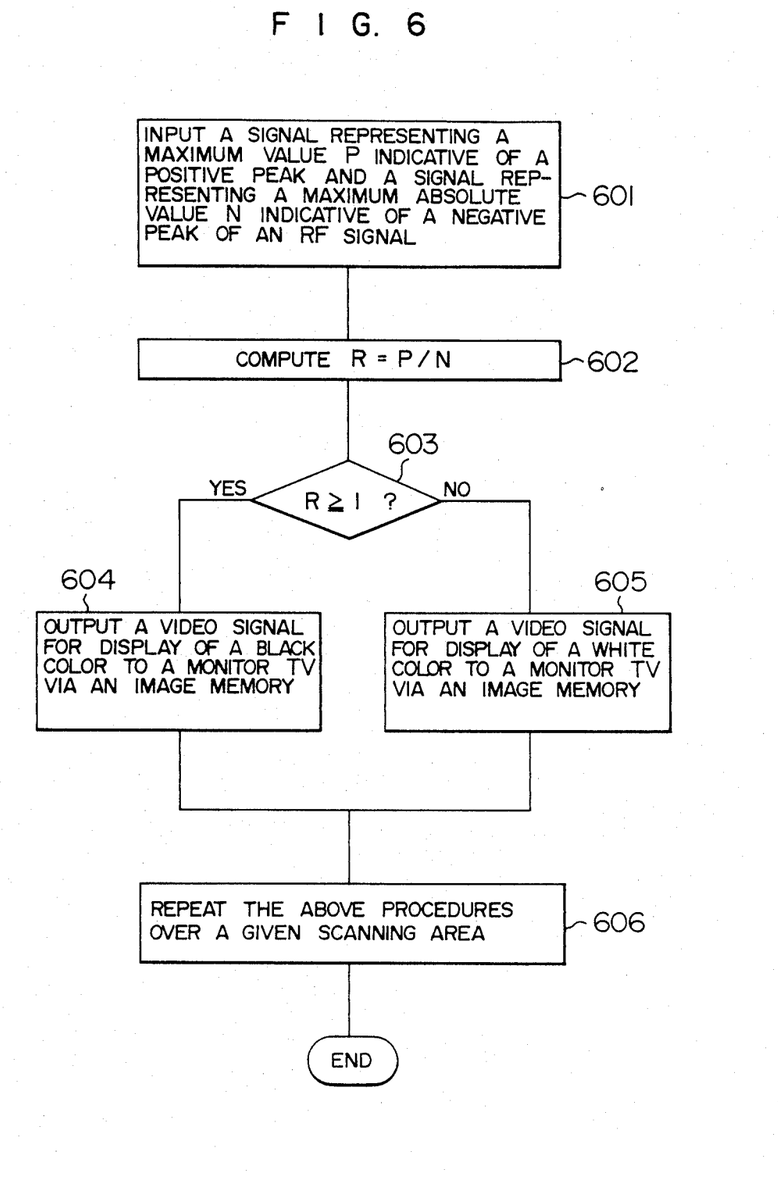
FIG. 6 is a flow chart similar to FIG. 2 but illustrating essential part of controlling performed by a CPU included in an ultrasonic inspection apparatus according to another embodiment of the invention.
Figure 7:
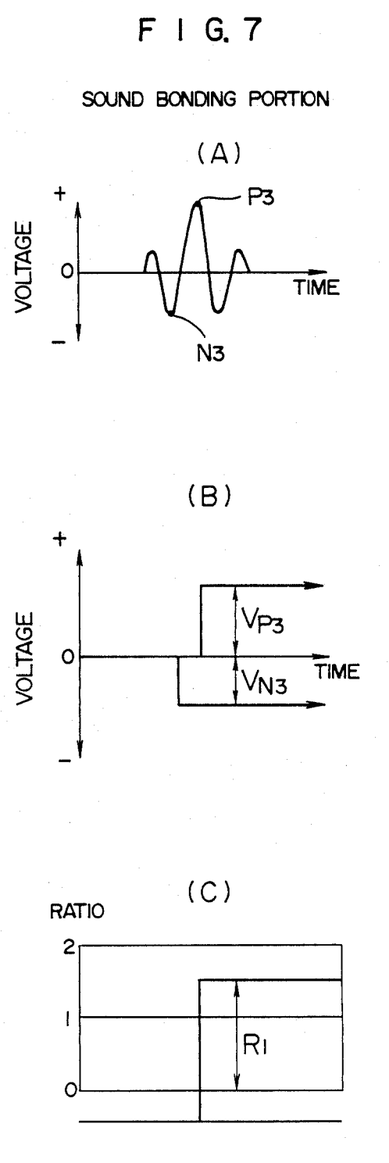
FIGS. 7(A)-7(C) illustrate an RF signal, a DC voltage output from the peak detector and a ratio computed by the CPU of the FIG. 6 apparatus which are obtained from a bonding portion without exfoliation of an object.
Figure 8:
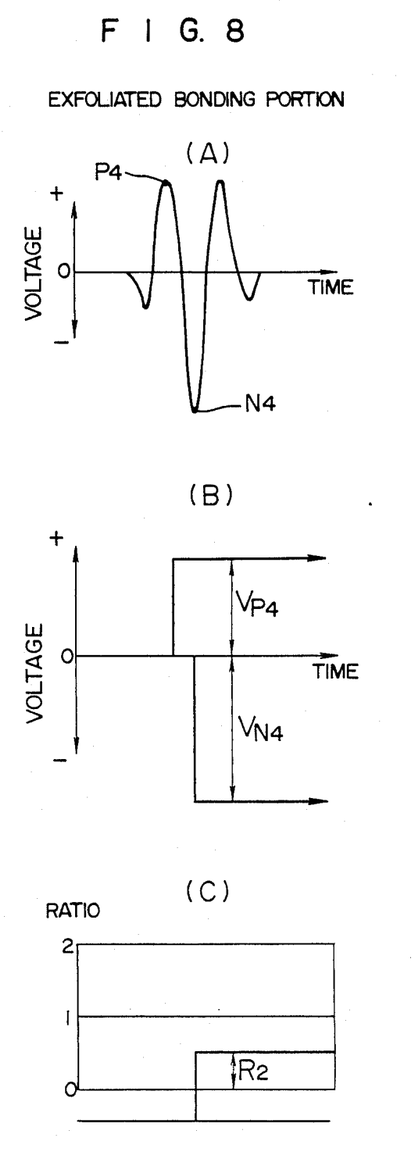
FIGS. 8(A)-8(C) illustrate waveforms similar to those of FIGS. 7(A)-7(C), but obtained from a bonding portion with exfoliation of an object.

To implement the ratio comparison with the ultrasonic inspection apparatus 1, the program of the CPU 10 may be modified as shown in FIG. 6 such that a signal representing a maximum value P indicative of a positive peak of an RF signal and a signal representing a maximum absolute value N indicative of a negative peak of the RF signal are inputted (step 601), R=P/N is then computed (step 602), judgement is executed as to whether the ratio R is larger than 1 or not (step 603), and a binary video signal corresponding to a value of the ratio R is delivered or a multi-coded video signal for gradation display depending and the value and the level of the ratio R. With the ultrasonic inspection apparatus modified as above, when an RF signal having a waveform in FIG. 7(A) is inputted, the peak detector 7 detects a maximum value P3 indicative of a positive peak and a maximum absolute value N3 indicative of a negative peak of the RF signal to produce DC voltages VP3 and VN3 which are, in FIG. 7(B), proportional to the maximum values, and the CPU 10 computes a ratio of VP3 to VN3 to provide a computed value R1 in FIG. 7(C). The CPU 10 then judges the computed value R1 as to whether it is larger than 1 (one) or not and produces a video signal in accordance with a value of R1 which is larger than one in this example. When an RF signal of a waveform in FIG. 8(A) is inputted, the peak detector 7 likewise detects two maximum values P4 and N4 to produce DC voltages VP4 and VN4 proportional thereto in FIG. 8(B) and the CPU 10 computes a ratio of P4 to N4 to provide a computed value R2. Then, the CPU 10 judges the computed value R2 as to whether it is larger than one and because of the R2 being less than one in FIG. 8(C), it produces a video signal which is different from the above-mentioned video signal. In this way, a C-scope display which is, for example, monochromatic as in the previous embodiment can be displayed on the monitor television and the inspector can examine the presence or absence of a defect with ease and quickness.

This embodiment, like the previous embodiment, may introduce a threshold α experimentally determined for each kind of object to be inspected to improve reliability of judgement of the presence or absence of a defect. To this end, the program of the CPU 10 may be modified such that R=(P/N)−α is computed.

When the threshold α is introduced into the subtraction computation between the maximum values P and N, these maximum values P and N are varied in level depending on not only the presence or absence of a defect such as exfoliation but also the other factors such as attenuation factor and transmission factor of the ultrasonic beam determined for a material of the object being inspected and a characteristic of the probe. This still requires that the threshold α must be changed in a very sophisticated manner to comply with variations in the other factors mentioned above. In computing the ratio of the maximum value P to the maximum value N according to the second embodiment, however, level variations due to the other factors than the presence or absence of a defect can advantageously be cancelled out and hence the same threshold α can always be used for the same kind of the object. From this standpoint, the second embodiment based on the ratio computation is considered to be more practical.

In the foregoing embodiments, either the computed difference between the positive peak maximum value and negative peak maximum absolute value of the RF signal or the computed ratio of the former to the latter is converted into the video signal and indicated as a display on the monitor television. Alternatively, the computed value may exemplarily be reconverted into an analog signal, and its level may be displayed on an oscilloscope. With this alteration, the inspector can likewise examine the presence or absence of a defect with ease and quickness by watching the oscilloscope.

As described above, in the ultrasonic inspection method and apparatus according to the invention, a computation is executed for comparing in magnitude a maximum value indicative of a positive peak with a maximum absolute value of a negative peak of an RF signal stemming from a reflection beam from an object to be inspected, and a computed value is displayed on the display unit and observed to check the RF signal for its phase inversion. Accordingly, the contents of display can be simplified and even an inexpert inspector can examine the presence or absence of a defect with ease and quickness.

We claim:

1. An ultrasonic inspection apparatus having a probe for emitting an ultrasonic beam to at least one kind of an object to be inspected, a pulser for transmitting to said probe a pulse signal necessary for generation of the ultrasonic beam, a receiver for receiving a reflection beam of said ultrasonic beam from said object and for generating an RF signal corresponding to said reflection beam, and display means for displaying data of said RF signal to allow a presence or absence of a defect in said object to be judged on a basis of contents displayed on said display means, said apparatus comprising:

a peak detector, connected to said receiver, for detecting a maximum value indicative of a positive peak and a maximum absolute value indicative of a negative peak of said RF signal; and control means, connected to said peak detector, for performing a computation for comparing in magnitude said maximum value indicative of the positive peak with said maximum absolute value indicative of the negative peak and transmitting a computed value to said display means to cause the computed value to be displayed thereon, wherein said peak detector comprises a first polarity circuit for passing only a positive-going waveform of said RF signal and a second polarity circuit for passing only a negative-going waveform, first and second detection circuits for respectively detecting the positive-going waveform passed through said first polarity circuit and the negative-going waveform passed through said second polarity circuit, and first and second hold circuits for respectively holding maximum values of said waveforms respectively detected by said first and second detection circuits thereby enabling said positive peak maximum value and negative peak maximum absolute value of said RF signal to be detected.

2. An ultrasonic inspection apparatus according to claim 1 wherein said display means is a monitor television connected to said control means, and said control means is operated to convert said computed value into a binary signal or multi-coded signal depending on a level thereof to allow said computed value to be displayed as a C-scope display on said monitor television.

3. An ultrasonic inspection apparatus according to claim 1 wherein said control means is operative to perform, as said computation a subtraction of said maximum absolute value indicative of the negative peak from said maximum value indicative of the positive peak.

4. An ultrasonic inspection apparatus according to claim 1 wherein said control means is operated to perform, as said computation a ratio computation of said maximum value indicative of the positive peak to said maximum absolute value indicative of the negative peak.

5. An ultrasonic inspection apparatus according to claim 3 wherein said control means is operative to produce a binary signal in accordance with a positive or negative polarity of said computed value or a multi-coded signal depending on a level of said computed value to cause a C-scope display on said monitor television on a basis of said binary or multi-coded signal.

6. An ultrasonic inspection apparatus according to claim 4 wherein said control means is operative to produce a binary signal in accordance with whether said computed value is greater than 1 (one) or not or a multi-coded signal depending on a level of the computed value to cause a C-scope display on said monitor television on a basis of said binary or multi-coded signal.

7. An ultrasonic inspection apparatus according to claim 1, wherein said control means performs said computation for comparing in magnitude a maximum value indicative of the positive peak with said maximum absolute value indicative of the negative peak and includes in said computation a predetermined threshold experimentally determined for each kind of object.

8. An ultrasonic inspection apparatus according to claim 1, wherein said control means performs a computation of a subtraction of a sum of said maximum absolute value and a threshold experimentally determined for each kind of object from said maximum value, whereby when the computed value is positive, a phase of said RF signal is judged not to be inverted and when negative, the phase of said RF signal is judged to be inverted.

9. An ultrasonic inspection apparatus according to claim 1, wherein said control means performs a computation including in combination a ratio computation of said maximum value to said maximum absolute value and a subtraction of a threshold experimentally determined for each kind of object from a computed ratio, whereby when the computed value is greater than one, a phase of said RF signal is judged not to be inverted and when less than one, the phase of said RF signal is judged to be inverted.

* * * * *